United States Patent [19]

Barken

[11] Patent Number: 5,531,742

[45] Date of Patent: Jul. 2, 1996

[54] APPARATUS AND METHOD FOR COMPUTER CONTROLLED CRYOSURGERY

[76] Inventor: Israel Barken, 6823 Deer Hollow Pl., San Diego, Calif. 92120

[21] Appl. No.: 821,492

[22] Filed: Jan. 15, 1992

[51] Int. Cl.⁶ ............................................. A61B 17/36
[52] U.S. Cl. .............................................................. 606/21
[58] Field of Search .................................. 128/399, 660, 128/660.1; 606/20–24, 26

[56] References Cited

U.S. PATENT DOCUMENTS

| | | | |
|---|---|---|---|
| 4,377,168 | 3/1983 | Rzasa et al. | 128/399 |
| 4,576,177 | 3/1986 | Webster, Jr. | 128/660 |
| 4,587,972 | 5/1986 | Morantte, Jr. | 128/660 |
| 4,672,963 | 6/1987 | Barken | 606/12 |
| 4,841,979 | 6/1989 | Dow et al. | 128/660.1 |
| 4,887,605 | 12/1989 | Angelsen et al. | 128/660.03 |
| 4,917,096 | 4/1990 | Englehart et al. | 128/660.1 |

*Primary Examiner*—William E. Kamm
*Attorney, Agent, or Firm*—David G. Rosenbaum

[57] ABSTRACT

A surgical system and method for destroying unwanted internal structures including a cryosurgery probe or probes, an ultrasonic or MRI robe and a computer system is described. The ultrasonic or MRI probe provides data signals that are processed by the computer system to provide an image of the structures involved in the freezing procedure. The cryosurgery probes can be inserted in the body and activated manually or by the computer system to provide freezing capable of destroying internal tissue. By calibrating the effects of the cryosurgery probe or probes as a function of power and duration, the surgical procedure can be controlled by including overlaying images of the regions already affected by the cryosurgery probe or probes on the images previously provided by the ultrasonic or MRI probe. This image reconstruction can be performed in real time providing immediate feedback to the attending physician. The computer system can also monitor system parameters such a freezing power and duration. This system has particular application to procedures involving the prostate gland where the cryosurgery probe or probes can be inserted intra-perineally and the ultrasonic probe or MRI can be inserted intra-perineally or trans-rectally.

12 Claims, 2 Drawing Sheets

APPARATUS AND METHOD FOR COMPUTER CONTROLLED CRYOSURGERY

BACKGROUND OF THE INVENTION

The invention relates generally to cryosurgery and more particularly to an automated and integrated system including a cryosurgery device, an imaging probe and a computer system for use in performing internal surgery. The attending physician provides input either directly or through the computer while watching a displayed image generated by the imaging probe onto a screen in "real-time." The real-time image will display the extent of tissue freezing with special attention to the border and limits of the desired tissue to be frozen. The physician may directly control, or have the computer system control the duration and the intensity of freezing with passible linkage to shutting of the process if certain predetermined criteria are not met.

The use of cryosurgery dates back to 1964 when Geonder et al. published "Experimental Prostatic Cryosurgery" in Investigative Urology 1:610–619. There is vast clinical accumulation of data on cryosurgery for cancer of the prostate as published by Dr. Loening from Iowa Medical School in the "UROLOGICAL CLINICS OF NORTH AMERICA" 1988.

A key advantage of cryosurgery is that it creates some immune response. Tissue destroyed by cryosurgery can typically be removed from the interior of the body by normal bodily processes. The freezing can be applied by established endo-techniques, such as those utilized in endo-urology, thus avoiding open surgery and enabling tissue destruction in areas where there is no easy access, or where opening of the skin and tissues is not desired.

Current research indicates a scientific interest in combining cryosurgery and ultrasound, in particular on the prostate gland. Onik G., et al, Urology 1991 Mar; 37 (3): 277–81 describe percutaneous transperineal prostate cryosurgery using trans-rectal ultrasound guidance.

Frozen tissue gives a distinct and typical ultrasonic signature. The distinct ultrasonic signature affords the ability to have a computer controlled check-and-balance of the procedure. Onik G., et al., Ultrasound Characteristics of Frozen Prostate, *Radiology* 1988, Sept: 168 (3): 629–31.

Magnetic resonance imaging (MRI) is a tissue imaging modality that utilizes computers to process magnetic signals and generate images. Castro D. J., MRI guided Nd:YAG interstitial laser Phototherapy (ILP) in an Ex-vivo Model: Dosimetry of Laser Tissue Interactions, *Lasers in Surgery and Medicine Supplement*, 3:6 1991.

A need has been felt for an apparatus and method for utilizing cryosurgery in a non-open surgical procedure that would permit precise definition of the region of tissue to be destroyed and in addition provide regional tissue definition by real time ultrasound picture or MRI.

SUMMARY OF THE INVENTION

It is therefore an object of the present invention to provide an improved technique for precise and controlled destruction of internal bodily structures.

It is a further object of the present invention to provide an improved technique for using cryosurgery to precisely locate and destroy unwanted internal tissue in the body.

It is another more particular object of the present invention to use the ultrasonic imaging technique or MRI visualization to control the positioning of the cryosurgery probe or probes to freeze predetermined structures during tissue destruction procedures. It is another more particular object to provide an apparatus and method for destroying a portion of or all of a prostate gland without utilizing the technique of open surgery.

The aforementioned and other objects are accomplished, according to the present invention, by monitoring the position of the cryosurgery probes, transmitting the freezing agents to selected internal structures and performing a controlled freezing of an internal tissue structure through the use of an ultrasonic probe, applied externally or internally, or through MRI externally or internally. The ultrasonic probe is coupled to a computer for providing a multiplicity of cross sectional images of the internal body structure which are compiled by the computer into a three dimensional image of the tissue structure. The images can be interpreted by a computer system in conjunction with the physician or manipulated manually by the physician at any portion of the procedure. The parameters controlled by either combination will include control of the freezing intensity, speed and time duration.

A non-limiting example of a cryosurgical technique contemplated by the present invention is use in conducting a prostatectomy, i.e., removal of the prostate gland. According to this technique the imaging probe is trans-rectally or intra-urethrally inserted into the patient or directly into the organ, i.e., interstitially. A second catheter may be used to carry the cryosurgical instrument, or the imaging probe and the cryosurgical instrument may be inserted through distinct lumens in a multi-lumened catheter. Where MRI is used, it can be applied externally or by MRI intra-rectal coil. These and other features of the present invention can be understood upon reading of the following description along with Figures.

DETAILED DESCRIPTION OF THE FIGURES

Figure 1:
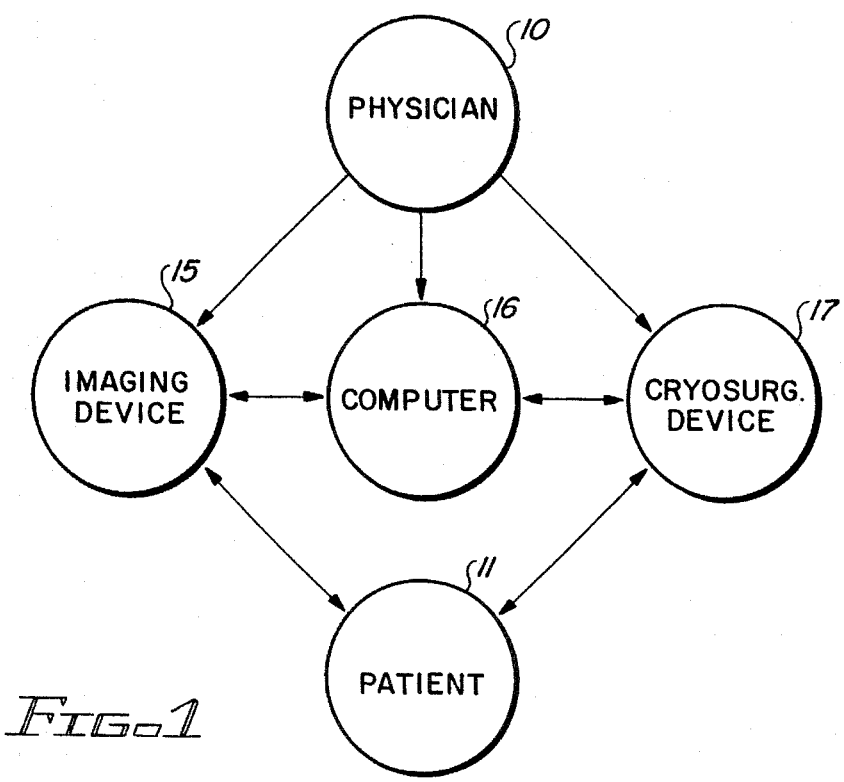
FIG. 1 is a general diagram illustrating the system for performing the surgical technique of the instant invention.
Figure 1A:
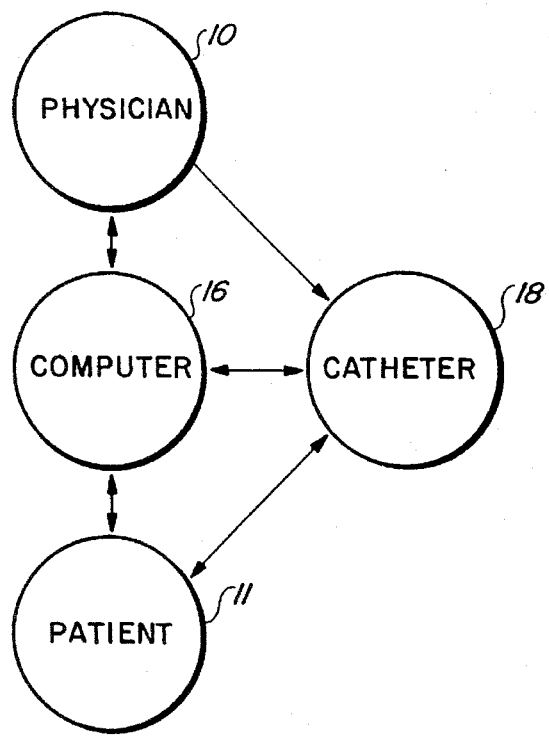
FIG. 1A is a general diagram illustrating the system for performing the surgical technique of the instant invention using a catheter for both imaging and cryosurgery.

Referring to FIG. 1, a general diagram of the computerized ultrasound cryosurgery system is shown. The physician 10 has at his disposal and under his control an imaging device 15, such as an ultrasound or MRI transceiver, a cryosurgery device 17 and a computer system 16. The imaging device 15 and the cryosurgery device 17 interact directly with the patient 11 as shown in FIG. 1 or are introduced into the patient using a catheter 18 as shown in FIG. 1A. The computer system 16 processes information from the imaging device 15 to provide an image on an associated monitor. In addition, the computer system 16 monitors and controls the activity (i.e. activation and power of the cryosurgery device 17). The physician 10 can enter data into the computer system 16 through an interactive display or any other mode. Control over both the imaging and the cryosurgical device 15,17 may be accomplished manually by the physician 10 or by interactive control with the computer 16. It will be clear that for other purposes such as monitoring bodily parameters, administering anesthesia, etc., the attending physician and or associated personnel can additionally interact with the patient 11.

Figure 2:
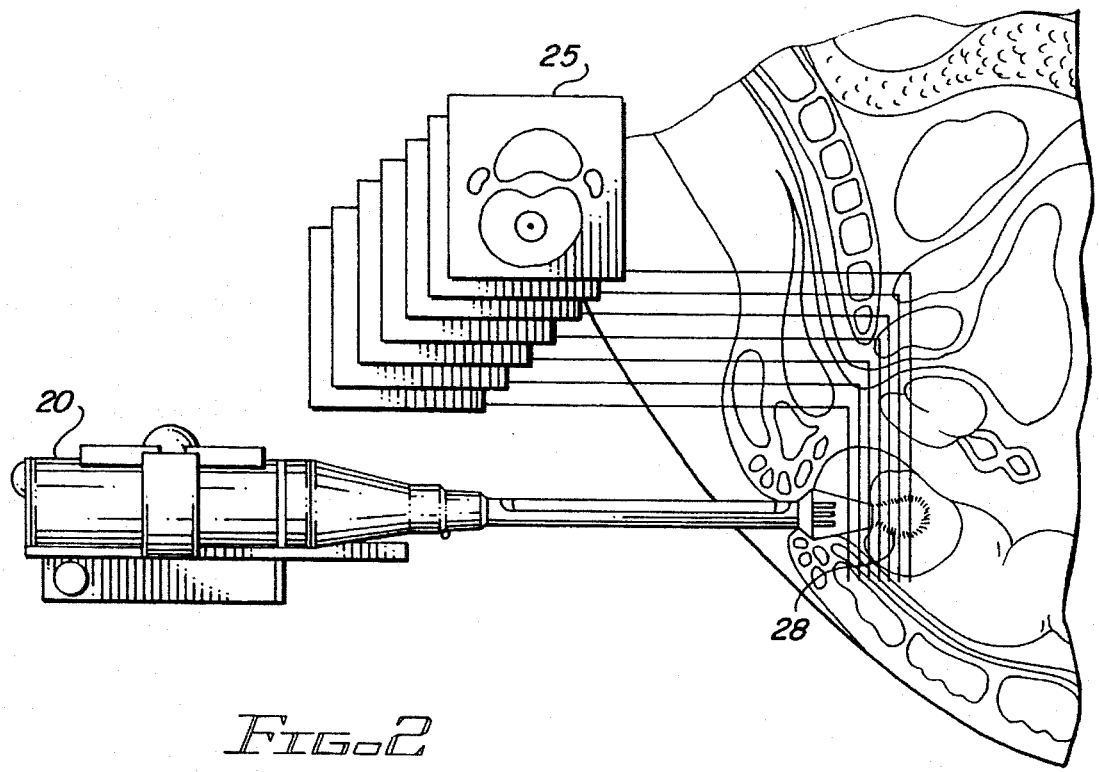
FIG. 2 is a schematic illustration of how the ultrasonic probe can provide a three dimensional image of an internal organ (e.g. the prostate gland).

Referring to FIG. 2, there is shown a schematic diagram of the reconstruction of an internal structure. The imaging device 20 is inserted into the patient 11 through a body opening, e.g., trans-rectally. Once inserted in the opening, a series of cross sectional images 25 can be provided that define the selected structure (e.g. the prostate gland 28) under investigation by knowing the relative location of the imagings probe in the body. Thus, the computer 16 can reconstruct a three dimensional image of the structure under investigation by accumulating planar images of known separation.

Figure 3:
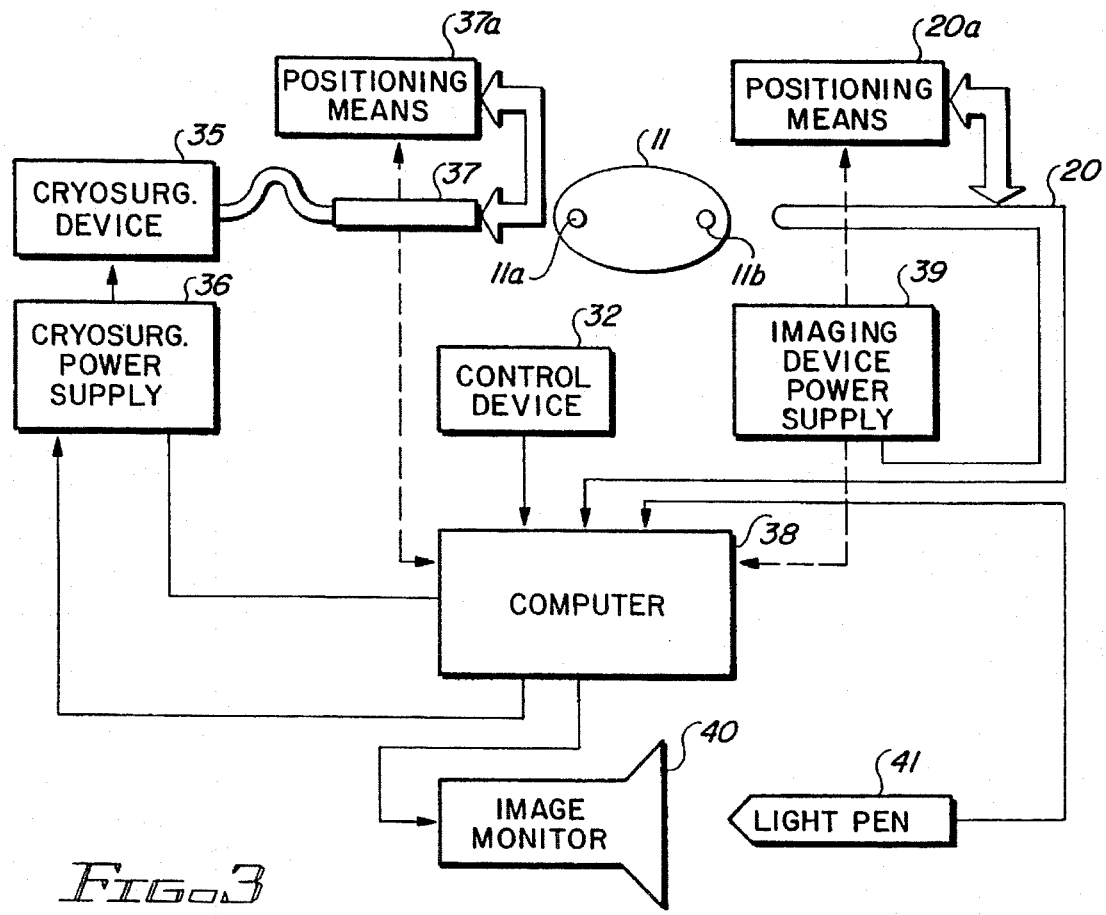
FIG. 3 is a schematic diagram of the use of an ultrasonic probe/MRI probe and a cryosurgery probe during a surgical procedure according to the instant invention.

Referring next to FIG. 3 a diagram of the present invention is shown. A power supply 36 controls the output of a cryosurgery device 35. The cryosurgery probe 37 is inserted into the body after an opening or openings 11a are created by known endo-urology techniques. The cryosurgery probe 37 is typically under the control, either directly, or indirectly of the attending physicians. An imaging device power supply 39 applies electrical signals into the ultrasonic/MRI transceiver 20 which is inserted into a second body opening (e.g. the rectal canal 11b) of the patient 11. The openings in the patient 11 are either natural ones or created by endo-urology techniques. The reflected waves from the ultrasonic probe are detected by the imaging device 20 after being processed by the computer system 28 and are transmitted to the image monitor 40. Monitor 40 may represent an MRI image. The monitor can provide a real time cross sectional image determined by the position of the imaging device 20. The motion of the imaging device 20 relative to patient 11 at the same time provides a facility for monitoring the image on the image monitor 40 through a light pen 41. The imaging device 20 is positioned by position means 20a and the cryosurgery probe is positioned by positioning means 37a. The position means 20a, 37a can be members of the medical staff and/or devices controlled by signals from the computer system 38. The imaging device power supply 39, the cryosurgery power supply 36 and the light pen 41 are controlled by a computer system 38 which, in turn, can be under the control of a control device 32. The computer system 38 is used to automate the surgical procedure to the maximum extent possible while still maintaining the control of the procedure by the attending physician. The physician can at all times override the computer 38 or use the systems manually.

Although the present invention has applicability to any non-open surgical procedure, the immediate anticipated use is for cryosurgical prostatectomies. Normal bodily function will cause sloughing of the dead tissue which is removed by the body. The prostate gland provides clearly definable ultrasonic/MRI image signature when viewed on a monitor while cryosurgery is applied. The prostate gland is important because benign prostatic hypertrophy affects every man above the age of 50 with clinical presentation at the age of 60. In addition, cancer of the prostate gland is the second largest killer of the U.S. male population. Furthermore, the prostate gland is relatively accessible through the natural opening of the urethra or the perineal skin. The surgical procedure involving removal by radical surgery of the prostate gland can have severe side effects. The relatively non-traumatic surgical technique of the instant invention, for partial or complete destruction with subsequent removal of the destroyed prostate gland by the body itself, minimizes the side effects and decreases the discomfort to the patient. The destroyed tissue will not normally be removed during performance of this procedure but is eliminated by normal body function.

The images of the ultrasound or MRI are inspected in real time by the physician. The prostate gland provides very distinctive tissue boarders, facilitating imaging and viewing of the tissue. The location of the cryosurgery probe or probes are also distinctively located. As soon as the freezing is applied, a shadowy ball (bypoechoic area) is seen and its margins are seen very clearly. Manual control over activation or deactivation of the freezing process may be used. Alternatively, a pen or other stylus may be used interactively with the imaging screen to allow the computer to control the activation and deactivation of the freezing process. The physician will have at all times the ability to override the computerized command or he will be able to activate the freezing directly through the touch screen and light pen or any other input means.

As with most computer systems, storage media will be provided for archival and historical saving of data for individual patient files, or to accumulate a data library of power and duration application of the freezing. The stored data library can then be subsequently used for automating the procedure.

The above description is included to illustrate the operation of the preferred embodiment and is not meant to limit the scope of the invention. The scope of the invention is to be limited only by the following claims. Many variations will be apparent to one skilled in the art that can yet be encompassed by the spirit and scope of the invention. For example, it will be clear to those skilled in the art that the ultrasonic/MRI probe, for some applications, does not need to be inserted within the body but can have the position varied in a known manner over an external area for investigation of certain bodily structures. In addition, relatively thin cryosurgery probes can be inserted into the body with a relatively small surgically created opening in the exterior of the body creating relatively minor trauma to the patient.

What is claimed is:

1. Apparatus for destroying unwanted internal tissue comprising:

imaging means for applying imaging signals to an internal body region of a patient, receiving the imaging signals and generating a real-time image of the internal body region of the patient;

cryosurgery means for freezing predetermined areas of said internal body region of said patient; and control means for controlling the cryosurgery means in conjunction with the imaging means.

2. Apparatus for destroying unwanted internal tissue as claimed in claim 1 wherein said imaging means further comprises one of ultrasound imaging or magnetic resonance imaging.

3. Apparatus for destroying unwanted internal tissue as claimed in claim 1 further comprising display means for receiving a representation of an image of the internal body region.

4. Apparatus for destroying unwanted internal tissue as claimed in claim 3, further comprising input means connected to said display means and responsive to said control means for receiving input from an operator to delimit healthy internal tissues from unwanted internal tissues, wherein said control means controls both an intensity and duration of freezing by said cryosurgery freezing means.

5. Apparatus for destroying unwanted internal tissue as claimed in claim 1, wherein said control means further comprises a computer processor.

6. Apparatus for destroying unwanted internal tissue as claimed in claim 5, wherein said imaging means further comprises a probing means for applying said imaging signals and a receiving means for receiving said imaging signals both located internally to the body of said patient, and wherein said computer processor further comprises disabling means for disabling said cryosurgery means when a position of said cryosurgery means is such as to freeze healthy tissue.

7. Apparatus for destroying unwanted internal tissues as claimed in claim 1, wherein said imaging means and said cryosurgery means comprise a unitary structure adapted to be inserted into the patient through one of a natural or surgically-created opening in the body.

8. A method for destroying unwanted internal tissue comprising the steps of:
 inserting a cryosurgery probe, capable of emitting a freezing output, through a bodily opening of a patient;
 imaging an area of unwanted internal tissue;
 determining a position of the cryosurgery probe relative to the unwanted internal tissue;
 providing substantially real-time image output from said imaging step to a computer means which controls a freezing output of the cryosurgery probe;
 inputting to the computer means, from an operator, information defining the internal tissue area to be destroyed;
 positioning the cryosurgery probe such that the freezing emanating from said cryosurgery probe will destroy only defined internal tissue identified by said inputting step;
 determining a power and duration of freezing to be applied to the defined internal tissue from the cryosurgery probe and controlling the power and duration of freezing emanating from said cryosurgery probe; and
 freezing said defined internal tissue with said cryosurgery probe, thereby destroying said defined internal tissue.

9. The method of destroying unwanted internal tissue, according to claim 8, further comprising the steps of:
 determining with said computer means if said power and duration of said freezing emanating from said cryosurgery probe will harm healthy tissue; and
 disabling said power and duration of said freezing emanating from said cryosurgery probe means if said step of determining yields a possibility of harm to healthy tissue.

10. The method according to claim 8, wherein said step of imaging the area of unwanted internal tissue is performed external to the patient's body.

11. The method according to claim 8, wherein said step of imaging the area of unwanted internal tissue is performed internally with respect to the patient.

12. A method for destroying unhealthy prostate gland tissue comprising the steps of:
 inserting a cryosurgery probe through an opening in a patient;
 inserting an imaging probe into the patient;
 determining a position of the cryosurgery probe relative to the prostate gland;
 providing output from said determining step to a computer processor;
 providing a display of tissue surrounding said prostate gland, and said cryosurgery probe within said patient;
 accepting input delimiting healthy internal tissue from said prostate gland or any other organ;
 positioning said cryosurgery probe such that freezing emanating from said cryosurgery probe will destroy said prostate gland tissue;
 computing optimum power and duration of freezing to be applied to said cryosurgery probe, said step of computing being done by said computer processor;
 controlling said power and duration of said freezing applied to said cryosurgery probe with said computer processor;
 determining with said computer processor if said power and duration of said freezing applied to said cryosurgery probe will harm healthy tissue;
 disabling said power and duration of said freezing applied to said cryosurgery probe if said step determining yields a possibility of harm to healthy tissue;
 freezing said prostate gland tissue with said cryosurgery probe, and thereafter providing a display of said prostate gland tissue, said display showing results of said step of freezing.

* * * * *